United States Patent
Noe et al.

(10) Patent No.: US 11,179,317 B2
(45) Date of Patent: Nov. 23, 2021

(54) COSMETIC PRODUCT IN THE FORM OF A FOAM AND MAKE-UP METHOD

(71) Applicant: LVMH RECHERCHE, Saint Jean de Braye (FR)

(72) Inventors: Brigitte Noe, Clery Saint Andre (FR); Yohann Bichon, Maisons-Alfort (FR); Naïma Chentoufi, Saint Jean de Braye (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 17 days.

(21) Appl. No.: 16/470,481

(22) PCT Filed: Dec. 26, 2017

(86) PCT No.: PCT/FR2017/053844
§ 371 (c)(1),
(2) Date: Jun. 17, 2019

(87) PCT Pub. No.: WO2018/122527
PCT Pub. Date: Jul. 5, 2018

(65) Prior Publication Data
US 2020/0113813 A1 Apr. 16, 2020

(30) Foreign Application Priority Data
Dec. 28, 2016 (FR) .................... 1663470

(51) Int. Cl.
*A61K 8/96* (2006.01)
*A61K 8/04* (2006.01)
*A61K 8/31* (2006.01)
*A61K 8/89* (2006.01)
*A61Q 1/02* (2006.01)
*A61K 8/26* (2006.01)
*A61K 8/41* (2006.01)
*A61K 8/895* (2006.01)

(52) U.S. Cl.
CPC .............. *A61K 8/965* (2013.01); *A61K 8/046* (2013.01); *A61K 8/31* (2013.01); *A61K 8/89* (2013.01); *A61Q 1/02* (2013.01)

(58) Field of Classification Search
CPC .......... A61K 8/965; A61K 8/046; A61K 8/31; A61K 8/89; A61K 2800/31; A61K 2800/48; A61K 2800/546; A61K 8/042; A61K 8/26; A61K 8/416; A61K 8/895; A61K 8/044; A61Q 1/02
See application file for complete search history.

(56) References Cited

U.S. PATENT DOCUMENTS

| | | | |
|---|---|---|---|
| 4,970,252 | A | 11/1990 | Sakuta et al. |
| 7,470,725 | B2 | 12/2008 | Schwertfeger et al. |
| 2009/0269374 | A1 | 10/2009 | Lee et al. |
| 2016/0143842 | A1 | 5/2016 | Struwe |
| 2016/0296436 | A1 | 10/2016 | Arnaud et al. |

FOREIGN PATENT DOCUMENTS

| | | |
|---|---|---|
| FR | 2873581 | 11/2006 |
| FR | 3014312 | 6/2015 |

OTHER PUBLICATIONS

International Search Report and Written Opinion issued for International Patent Application No. PCT/FR2017/053844, dated Apr. 19, 2018, 28 pages including English translation.
MINTEL Record ID: 10174267, Date Published: Jun. 2004, Maybelline: "Dream Matte Mousse Foundation," (3 pages).
Database GNPD [Online] MINTEL; May 1, 2013, Ellis Faas: "Creamy Eyes Liquid Eyeshadow," XP002771990, Database accession No. 2054330 (5 pages).
Database GNPD [Online] MINTEL; Jul. 1, 2015, Deborah: "Watery Mousse Eyeshadow," XP002771991, Database accession No. 3250019 (4 pages).
Database GNPD [Online] MINTEL; Jun. 1, 2016, Johnson & Johnson: "Actif Unify Tinted Mousse Sunscreen SPF 30," XP002771992, Database accession No. 4046365 (4 pages).
Database GNPD [Online] MINTEL; Apr. 1, 2016, Botica Comercial Farmaceutica: "Matte Lip Colour Mousse," XP002771993, Database accession No. 3911397 (4 pages).
Database GNPD [Online] MINTEL; Oct. 1, 2016, Oriflame: "Matte Mousse," XP002771994, Database accession No. 4374587 (4 pages).
"Formulation Possibilities with new Silicone Elastomer Gel," IP.com Journal, IP.com Inc., West Henrietta, NY, US, Nov. 18, 2016, XP013173630, ISSN: 1533-0001 (16 pages).
"Gransil PC-12 Product Information," Oct. 1, 2012, XP055389790, Retrieved from the Internet: URL: https://www.ulprospector.com/documents/1030814.pdf?bs=4034&b=115740&st=1&sl=47758516&crit=a2V5d29yZDpbZ3JhbnNpbCBwYy0xMI0=&k=gransil:pc-12&r=eu&ind=personalcare [retrieved on Jul. 11, 2017] (1 page).

*Primary Examiner* — Trevor Love
(74) *Attorney, Agent, or Firm* — Hamre, Schumann, Mueller & Larson, P.C.

(57) ABSTRACT

The invention relates to a foundation with a foam texture which is stable over time, comprising a silicone gel and an organomodified clay forming a three-dimensional network in a mixture of a large proportion of volatile oils.

7 Claims, No Drawings

COSMETIC PRODUCT IN THE FORM OF A FOAM AND MAKE-UP METHOD

The present invention relates to a cosmetic composition with a particularly firm and light texture containing a silicone gel, an organomodified clay and a large proportion of volatile oils. The invention more particularly relates to the field of caring for and making up the skin.

The invention also relates to a cosmetic makeup or care process comprising the application of this composition to the skin.

PRIOR ART

The cosmetic products used as makeup base or as foundation essentially have the functions of hiding skin imperfections, unifying the complexion, obtaining a smoother skin appearance and improving the radiance of the complexion. To achieve these objectives, they contain solid particles such as colored pigments, diffusing compounds, reflective compounds and matt-effect or haze-effect compounds.

Fluid foundations comprise a dispersion of solid particles in liquids such as water and oils for easier application to the skin. Increasing the amount of solid particles which generate optical effects in this type of architecture makes it possible, admittedly, to improve the efficiency of the product, but gives rise to two problems. The sensation of lightness and of comfort on the skin is reduced, and it becomes difficult to ensure the homogeneity and stability of the texture. The formulator consequently makes use of surfactants, waxes or gelling agents, the function of which is to thicken it. However, these fluid foundation stabilizers impair the sensory properties of the product.

It is also proposed to formulate particles with an optical effect in a solid rather than a liquid fatty base. However, solid textures have the drawback of being much more difficult to spread, and nonuniform areas of product deposition often form on the skin, with the result that it is necessary to work the product on the skin for quite a long time to obtain a uniform makeup result.

To overcome these various drawbacks, textures with a consistency intermediate between that of fluid foundations, presented usually in a pump-dispenser bottle, and that of cream foundations, presented in a jar, have been proposed. Some of these textures are in the form of foams, obtained by introducing a gas in high proportions into a water-based fluid composition, which makes it possible to lighten the texture thereof (US 2016/0143842 is an illustration thereof). However, the introduction of a gas makes their manufacturing process more complex and reduces the stability of the product over time. These foams moreover leave a rather heavy film on the skin after application.

Foams containing a combination of several silicone elastomers, notably compounds known as dimethicone/vinyldimethicone crosspolymers, which are moreover useful for hiding wrinkles and smoothing the skin, have also been proposed previously. These formulations however contain nonvolatile hydrocarbon-based oils, and their texture is heavy on application and leaves a deposit on the skin that is quite present and sparingly comfortable, which is unsatisfactory when what is desired is, on the contrary, a light application which covers from the first few, or even from the very first, spreading action(s).

The need consequently remains for a skin makeup or care product which can reconcile a light and soft texture; an application which does not require excessive working on the skin; the incorporation of large amounts of solid particles to obtain efficient masking of skin imperfections; good stability; and a manufacturing process that is easy to perform and notably comprises a limited number of steps.

One object of the invention is to dispense with film-forming compounds that are felt to be present on the skin after application and that impair comfort of the worn product over time.

Another of its objects is to propose a cosmetic product whose texture is close to that of a foam and whose application on the skin is felt as being glidant, light and non-greasy. The makeup result that is obtained with this product must also allow very good coverage of imperfections and leave a powdery finish on the skin.

These objectives are achieved by the combination of two particular oil-gelling agents, which make it possible to integrate larger amounts of volatile oils and of solid particles than those implemented hitherto, in a texture that is stable, of high viscosity and very light at the same time, and the application of which affords a uniform deposit from the very first application.

DESCRIPTION OF THE INVENTION

A first subject of the present invention is thus a cosmetic composition for caring for or making up the skin, comprising:
from 35% to 75%, preferably from 60% to 70%, of at least one volatile oil,
from 1% to 6% of at least one crosslinked silicone polymer obtained by reaction of an organopolysiloxane comprising at least one —Si—H group in the end position with an organopolysiloxane comprising at least two vinyl groups, preferably located in the end position,
from 0.5% to 5% of an organomodified clay, and
less than 5% of water, the percentages being expressed on a mass basis relative to the mass of said composition.

The specific combination of two oil-gelling agents forms a novel texture, in the form of a foam, without it being necessary to necessarily introduce therein a gas, which simplifies the preparation process thereof and makes it possible to dispense with structuring compounds which give a heavy or greasy sensation on the skin.

In the continuation of the text, the percentages are expressed on a mass basis relative to the total mass of the composition of the invention, unless explicitly mentioned otherwise.

Definitions

In the present patent application, the expressions "from . . . to . . . " and "between . . . and . . . " are directed toward understanding the lower and upper limits of the range of values. The disclosure of a range of values excluding its limits amounts to disclosure of the equivalent range of values including the limits and vice versa.

The terms "crosslinked silicone polymer" and "silicone polymer" will be used equivalently in the present description.

For the purposes of the present invention, an "oil" may be defined as a water-insoluble compound (solubility of less than 0.05 mg/l at 20° C.), for which the melting point, the softening point or the glass transition temperature at atmospheric pressure is less than or equal to 30° C., preferably less than or equal to 25° C.

An oil of volatile nature may be defined by at least one of the criteria defined below.

The volatility may be defined in the context of the invention, for example a vapor pressure measurable by an empirical method at 25° C., and the value of which will be between 0.13 Pa and 40 000 Pa, for example between 1 Pa and 20 000 Pa, between 10 Pa and 8000 Pa, or even between 15 and 150 Pa. The vapor pressure will be measured according to one of the methods that are the best suited for the compound of interest, these methods featuring in the guidelines of Test No. 104 of the OCDE (2006 version). Alternatively, a volatile oil with a boiling point at atmospheric pressure of less than 250° C., preferably less than 230° C. and preferably between 150° C. and 220° C. may be chosen. Finally, the volatile oil may also be defined as an oil with a flash point ranging from 35° C. to 100° C., preferably between 40° C. and 80° C.

For example, a volatile oil such as isododecane will have a boiling point at $10^5$ Pa of between 175° C. and 195° C., a flash point of 45° C. and a vapor pressure at 20° C. equal to 100 Pa. Its solubility in water at 20° C. is less than or equal to $1.0 \times 10^{-2}$ mg/l.

Another volatile oil such as cyclopentadimethylsiloxane has a solubility in water at 25° C. equal to $1.7 \times 10^{-2}$ mg/l, a flash point of 77° C., a boiling point at $10^5$ Pa equal to 205° C., and a vapor pressure equal to 26 Pa at 25° C.

Crosslinked Silicone Polymer

The crosslinked silicone polymer may be non-gelled or gelled with a solvent for said polymer. It is preferable for it to be in the form of gelled or non-gelled particles whose mean size is between 10 and 200 microns. The crosslinked silicone polymer may be denoted as being a silicone elastomer by a person skilled in the art.

In the present description, the expressions "gelled or non-gelled crosslinked silicone polymer" and "gelled or non-gelled crosslinked silicone polymer particles" will be used equivalently. It is understood that "gelled" denotes "gelled with a solvent for the polymer". The expression "crosslinked silicone polymer" may denote the gelled or non-gelled crosslinked silicone polymer.

The present patent application also describes a gelled or non-gelled crosslinked silicone polymer which may be obtained by reaction of an organopolysiloxane preferably containing at least one —Si—H group in an end position with an organopolysiloxane comprising at least one, preferably at least two, ethylenically unsaturated groups linked to a silicon atom. The ethylenically unsaturated group may be chosen from vinyl, allyl and propenyl groups; it is preferably located at the ends of the organopolysiloxane molecule.

The crosslinked silicone polymer may be obtained by hydrosilylation reaction of the two organopolysiloxanes mentioned previously, in the presence of a catalyst and of an oil, under reaction conditions known to those skilled in the art. The catalyst may be hexachloroplatinic acid, or a platinum complex.

Alternatively, use may be made of a crosslinked silicone polymer obtained by dehydrogenation crosslinking condensation reaction between the two organopolysiloxanes described previously, in the presence of a catalyst and of an oil.

The oil used for the preparation of the crosslinked silicone polymer may be a nonvolatile oil or a volatile oil identical to one of the volatile oils described below included in the composition of the product of the invention. Mention will be made of isododecane or decamethylcyclopentasiloxane as solvent.

It is preferable for at least one of the organopolysiloxanes mentioned previously to predominantly comprise dimethylsiloxane units, the other units possibly being methylphenylsiloxane or dimethylvinylsiloxy units for a vinyl organosiloxane, and methylhydrogenosiloxane units for the organopolysiloxane containing —Si—H groups.

The organopolysiloxane comprising at least one ethylenically unsaturated group linked to a silicon atom may be chosen from copolymers of which some of the units comprise vinyl groups or for which at least one vinyl group is at the end of a chain.

The organopolysiloxane comprising at least one vinyl group may be chosen from methylvinylsiloxane/dimethylsiloxane copolymers, dimethylvinylsiloxy-terminated polydimethylsiloxanes, dimethylvinylsiloxy-terminated dimethylsiloxane/methylphenylsiloxane copolymers, and trimethylsiloxy-terminated dimethylsiloxane/methylvinylsiloxane copolymers.

The organopolysiloxane containing —Si—H groups and the organopolysiloxane comprising at least two vinyl end groups are preferably used in proportions such that the mole ratio between the total amount of hydrogen atoms linked to silicon atoms and the total amount of vinyl groups is between 1.5/1 and 20/1.

The organopolysiloxane containing —Si—H groups may be a polydimethylsiloxane or a poly(dimethyl)(methylhydrogeno)siloxane, one or the other comprising at least one Si—H bond at the end of a chain, preferably two Si—H bonds at the end of a chain.

Thus, the crosslinked copolymers obtained from an organopolysiloxane not containing any —Si—H groups at the end of a chain such as trimethylsilyl-terminated methylhydrosiloxane dimethylsiloxane copolymers, an INCI name of which may be Dimethicone/Vinyldimethicone Crosspolymer and which are sold, for example, under the brand name KSG®, do not form part of the present invention. The inventors have shown that these polymers not lead to a thick, glossy and unstable product.

In one embodiment, it is preferred for the second organopolysiloxane to be a dimethicone derivative and for the crosslinked polymer not to be obtained by reaction of a methicone silsesquioxane, as first organopolysiloxane. Such a polymer may correspond, in point of fact, to a compound whose INCI name is Vinyl Dimethicone/Methicone Silsesquioxane Crosspolymer, which may be found commercially notably under the reference KSP-100®.

The crosslinked silicone polymer is, for example, the product of reaction of a polydimethylsiloxane or of a poly(dimethyl)(methylhydrogeno)siloxane, one or the other comprising at least one Si—H end bond, with a polydimethylsiloxane comprising two vinyl groups (more specifically vinyldimethyl groups), preferably located in the end position of the chain.

Such a polymer is available under the brand name Gransil®, for example the product Gransil® PC-12.

It is preferred for the second organopolysiloxane not to comprise any vinylmethylsiloxane units, so that the polymer comprises only two vinyl groups located at the end of a chain.

The crosslinked silicone polymer is preferably in the form of a gel in the composition.

For example, the silicone polymer gel comprises gelled crosslinked silicone polymer particles trapping molecules of a solvent, which solvent represents between 10% and 95% by mass of the mass of the gel. The proportion of solvent contained in the gel may range from 60% to 95% by weight, for example from 80% to 90% by weight. Such a crosslinked silicone polymer gel may be manufactured by applying a high shear to crosslinked silicone polymer particles (which have been synthesized beforehand from the two organopolysiloxanes described previously), said shear being exerted in the presence of a solvent for the crosslinked silicone polymer. The shear may be produced in a high-pressure homogenizer, so as to obtain polymer particles gelled with said solvent; their size may range between 10 and 200 microns. This will be referred to equivalently as a crosslinked silicone polymer gel in a solvent or as crosslinked silicone polymer particles gelled with a solvent.

The solvent which gels the crosslinked silicone polymer particles may be a nonvolatile oil or, preferably, a volatile oil chosen from hydrocarbon-based volatile oils, silicone volatile oils or a mixture thereof, these oils being in accordance with the description of volatile oils given later.

Crosslinked silicone polymers whose INCI name corresponds to Polysilicone-11 may be used, and it is preferred to use Polysilicone-11 which is in a form gelled with isododecane, before its mixing with the other ingredients of the composition, and/or in the composition thus obtained.

A person skilled in the art will be able to confirm via conventional methods that the crosslinked silicone polymer is in the form of a gel in the composition.

When the crosslinked silicone polymer is in the form of a gel, the amount of crosslinked silicone polymer present in the composition may be expressed as the equivalent amount of polymer, it being understood that it would not be gelled in the absence of the solvent contained in the gel. Alternatively, the amount of crosslinked silicone polymer present in the composition may correspond to the amount of gel in the composition.

The equivalent amount of polymer of the gelled polymer advantageously ranges from 1% to 6% by weight of crosslinked silicone polymer relative to the weight of the care or makeup composition of the invention. This percentage is equivalent to the percentage of crosslinked silicone polymer if it were not gelled in the composition. The equivalent amount of non-gelled crosslinked silicone polymer is preferably between two values chosen from the group consisting of 1%, 1.5%, 2%, 2.5%, 3%, 3.5%, 4%, 4.5%, 5%, 5.5% and 6%.

The amount of gel containing the crosslinked silicone polymer gelled with a solvent is preferably between two values chosen from the group consisting of 20%, 22%, 24%, 26%, 28%, 30%, 32%, 34%, 36%, 38%, 40%, 42%, 44%, 46%, 48% and 50%.

The present patent application describes a crosslinked silicone polymer obtained by reaction of a trimethylsiloxy-terminated polymethylhydrogenosiloxane or of a trimethylsiloxy-terminated poly(dimethyl)(methylhydrogeno)siloxane with a polydimethylsiloxane comprising two vinyl groups, for example two vinyl end groups (i.e. dimethylvinylsiloxy-terminated polydimethylsiloxane), in the presence of a platinum catalyst. Some of these compounds are described in U.S. Pat. No. 4,970,252.

Organomodified Clay

The composition of the invention may contain from 0.5% to 5% by mass of an organomodified clay. The organomodified clay is, for example, an organomodified hectorite modified with a quaternary alkylammonium chloride, preferably an ammonium substituted with at least one, preferably at least two alkyls comprising from 14 to 20 carbon atoms. The alkyl may be stearyl. Mention will be made of the compound whose INCI name is disteardimonium hectorite in which the ammonium comprises two methyls and two stearyls.

The proportion of modified clay may be between two values chosen from the group consisting of 0.5%, 1%, 1.5%, 2%, 2.5%, 3%, 3.5%, 4%, 4.5% and 5%.

According to one embodiment, the composition comprises from 1% to 3% by mass of a hectorite modified with a quaternary stearyl ammonium chloride.

Volatiles

The volatile oils that are used in the composition of the invention are preferably branched-chain saturated hydrocarbons or silicones.

The volatile oil may be notably chosen from silicone oils such as dimethicones (polydimethylsiloxanes) whose viscosity ranges from 0.5 to 6 cSt and cyclodimethicones.

The volatile oil may be isohexyl neopentanoate or a hydrocarbon such as isododecane, isodecane, isohexadecane, n-dodecane (C12) and n-tetradecane (C14), or an undecane-tridecane mixture.

Mention will be made, for example, of octamethylcyclotetrasiloxane, decamethylcyclopentasiloxane, dodecamethylcyclohexasiloxane, heptamethylhexyl-trisiloxane, heptamethyloctyltrisiloxane, hexamethyldisiloxane, octa methyl-trisiloxane, decamethyltetrasiloxane, dodecamethylpentasiloxane, and mixtures thereof.

A volatile oil may be isododecane.

According to a particular embodiment of the invention, the composition of the invention contains at least two volatile oils chosen from alkanes and cyclomethicones, for example decamethylcyclopentasiloxane and isododecane.

It is preferred for isododecane to be predominant in a mixture of volatile oils, or for it to be the only volatile oil of the composition.

In a particular embodiment, the volatile oils contained in the composition preferably consist of a mixture of isododecane and of decamethylcyclopentasiloxane in a mass ratio of between 1/1 and 3/1, for example of the order of 2/1.

Other volatile oils such as those described in patent application FR 2873581 may also be used in the context of the present invention.

The proportion of volatile oils in the composition is preferably between 35% and 75%, more preferably between 60% and 70% by mass relative to the mass of the composition. The proportion of volatile oils may be between two values chosen from the group consisting of 35%, 40%, 45%, 50%, 55%, 60%, 65%, 70% and 75%.

Viscosity, Density and Stability

The viscosity of the composition at 25° C. and atmospheric pressure is preferably between 50 000 and 500 000 mPa·s, preferably between 80 000 and 300 000 mPa·s.

This viscosity may be measured using a Rheolab QC viscometer (Anton Paar) equipped with the Rheoplus software, using a suitable spindle and a suitable measuring time, for example under the following conditions:

| Geometries | Spin speed (rpm) | Measuring time (min) |
| --- | --- | --- |
| Coaxial cylinder: CC27 | 200 | 3 |
| 4 blades: ST22-4V | 100 | 3 |
| Fin: ST24-2D-2V-2V | 50 | 3 |
| Anchor: ST22-2V | 10 | 7 |

Prior to the measurement, the composition of the invention is placed in a 120 ml jar (Kola Rond VT3 M120 Blanc Pharm) in an oven at 25° C. for a minimum of 12 hours. Once the spindle has been inserted in the jar, the level of composition must reach the neck of the jar.

The correct choice of spindle is checked by measuring the percentage of deviation of the measurements, which are taken every 6 seconds. The viscosity value of the composition is equal, according to this protocol, to the average of the last fifteen measurements taken by the machine over the measuring time indicated above.

The density of the composition at 25° C. and atmospheric pressure is preferably between 0.8 and 1.2 g/cm³, for example from 0.85 to 1.15 and preferably between 0.9 and 1 g/cm³. It may be measured according to a method known to those skilled in the art.

The composition of the invention is advantageously stable, in the sense that it does not decant over time and conserves its light texture. The stability may thus be checked by a visual inspection after storage of the composition in an oven at 50° C., 45° C. or 4° C. for 1 or 2 months.

The composition preferably concurrently has the following properties: stable with a viscosity at 25° C. and atmospheric pressure of between 50 000 and 350 000 mPa·s, and a density at 25° C. and atmospheric pressure of between 0.8 and 1.2 g/cm³.

According to one embodiment of the invention, the composition has a viscosity at 25° C. and atmospheric pressure of between 200 000 and 250 000 mPas·s, a density at 25° C. and atmospheric pressure of between 0.9 and 1.0 g/cm³ and comprises, besides the crosslinked silicone polymer and the organomodified clay, from 35% to 75%, preferably from 60% to 70%, by mass of at least one volatile oil, and from 10% to 30% by mass of solid particles.

The mixture of the oils contained in the composition, notably the volatile oils and optionally the nonvolatile oils, preferably has a density at 25° C. and atmospheric pressure of less than 0.9 g/cm³, preferably less than 0.85 g/cm³, or even less than 0.8 g/cm³ and greater than 0.7 g/cm³.

Combination of Silicone Polymer and Clay

In a particular embodiment, the silicone polymer is a polysilicone-11 and the organomodified clay is an organomodified hectorite.

The mass ratio between the non-gelled crosslinked silicone polymer, for example polysilicone-11, and the organomodified clay, for example modified hectorite, is preferably between 1/1 and 10/1.

In particular, a composition having at least one of the following characteristics, for example one, two or three of the following characteristics, is preferred:
- a mass ratio between the non-gelled crosslinked silicone polymer between two values chosen from the group consisting of 1/1, 2/1, 3/1, 4/1, 5/1, 6/1, 7/1, 8/1, 9/1 and 10/1. For example, the mass ratio is greater than or equal to 18/10, 19/10, 2/1, 21/10, 22/10, 23/10 and 24/10 and 25/1,
- an amount of non-gelled crosslinked silicone polymer between two values chosen from the group consisting of 1%, 1.5%, 2%, 2.5%, 3%, 3.5%, 4%, 4.5%, 5%, 5.5% and 6%,
- an amount of crosslinked silicone polymer gelled with a solvent, preferably a volatile oil mentioned previously, between two values chosen from the group consisting of 20%, 22%, 24%, 26%, 28%, 30%, 32%, 34%, 36%, 38%, 40%, 42%, 44%, 46%, 48% and 50%,
- an amount of modified clay between two values chosen from the group consisting of 0.5%, 1%, 1.5%, 2%, 2.5%, 3%, 3.5%, 4%, 4.5% and 5%, the percentages being expressed on a mass basis relative to the mass of the composition.

In particular, the patent application describes a composition whose dynamic viscosity at 25° C. and atmospheric pressure is preferably between 50 000 and 350 000 mPa·s containing from 35% to 75% by mass of at least one volatile oil, from 1% to 6% by mass of polysilicone-11, from 0.5% to 5% by mass of a modified hectorite, and less than 5% by mass of water.

Solid Particles

It is advantageously possible to incorporate into the mixture of volatile oil, of crosslinked silicone polymer and of organomodified clay, as are described previously, solid particles such as pigments and fillers so as to obtain optical effects, such as color, reflection of light or scattering of light. As opposed to a pigment, a filler is colorless.

The composition of the invention advantageously contains solid particles which have particular optical properties.

The solid particles with an optical effect, as defined in the present invention, may be particles which absorb visible light, thus producing a color effect, such as pigments and nacres, particles with high diffuse reflectance, low specular reflection and high diffuse transmittance, commonly known as soft-focus particles, and haze-effect or matt-effect particles which reduce the gloss by absorbing sebum.

Among the mineral pigments, examples that may be mentioned include titanium dioxide, optionally surface-treated; black, yellow, red and brown iron oxides; manganese violet; ultramarine blue; chromium oxide; chromium oxide hydrate; carbon black and ferric blue.

Among the organic pigments, examples that may be mentioned include the pigments D & C Red No. 19; D & C Red No. 9; D & C Red No. 21; D & C Orange No. 4; D & C Orange No. 5; D & C Red No. 27; D & C Red No. 13; D & C Red No. 7; D & C Red No. 6; D & C Yellow No. 5; D & C Red No. 36; D & C Orange No. 10; D & C Yellow No. 6; D & C Red No. 30; D & C Red No. 3.

Use may also be made of interference pigments, such as nacres, which are capable of producing a color by an interference phenomenon, by reflection of light by superposed layers of materials with different refractive indices. The nacreous pigments may be chosen notably from white nacreous pigments, such as mica coated with titanium oxide, bismuth oxychloride; and colored nacreous pigments such as titanium mica with iron oxides, titanium mica with ferric blue or with chromium oxide, titanium mica with an organic pigment of the abovementioned type, and also pigments based on bismuth oxychloride.

Examples of haze-effect and/or matt-effect powders (also known as fillers) comprise alumina, silica, aluminum silicate, fumed silica, silica silylate, titanium dioxide or sericite powders. Fillers with a particle size of less than 20 microns, and of organic nature such as talc-titanium dioxide/alumina/silica composite powders, polyamide (Nylon 12) powders, polymethyl (meth)acrylate (hollow PMMA spheres), acrylate/styrene copolymers, hexyldecyl diisocyanate trimethylol hexyl lactone crosspolymer, micronized PTFE, synthetic fluorophlogopite and boron nitride, may be used in the context of the invention.

It is preferred in the context of the invention not to use particles containing —OH groups, such as untreated silica, for example. It will consequently be preferred to use silicas for which the surface —OH groups have been modified, such as silica dimethyl silylate and silica silylate.

The solid particles are advantageously contained in the composition of the invention in amounts of between 10% and 30% by mass, for example between 15% and 25% by mass. The mass ratio between the solid particles and the crosslinked silicone polymer is preferably between 4/1 and 6/1. It is, for example, of the order of 5/1.

The composition may comprise from 3% to 12% by mass of fillers and from 8% to 15% of pigments.

Additional Ingredients

An amount of polymer which gives film-forming properties to a deposit of the composition on the skin, and which is intended to increase the persistence of the film of composition on the skin, may be incorporated into the composition of the invention. The amount of polymer ranges, for example, from 1% to 10% by mass, more preferably from 3% to 7%, or even from 4% to 6%, relative to the mass of the composition.

According to one embodiment of the invention, a silicone resin is used as film-forming polymer.

A composition according to the invention may comprise as film-forming polymer at least one silicone resin chosen from the group consisting of silicone resins comprising at least one unit chosen from the units M (trialkylSiO$_{1/2}$), D (dialkylSiO$_{2/2}$), T (alkylSiO$_{3/2}$) and Q (SiO$_{4/2}$).

As examples of solid silicone resins of MQ type, mention may be made of trimethyl siloxysilicates phenylalkyl siloxysilicates, such as phenylpropyldimethyl siloxysilicate.

The composition may contain from 1% to 10% by mass of a silicone resin, preferably from 1% to 10% by mass of a trimethyl siloxysilicate resin, relative to the mass of said composition.

Silicone resins comprising units T and optionally D units may be polysilsesquioxanes optionally comprising Si—OH end groups. Preferably, use may be made of polymethylsilsesquioxane resins.

Mention may also be made of resins comprising M, Q and T units, such as MQT-propyl resins.

Any other film-forming polymer known to a person skilled in the art which is soluble in the volatile oil or the mixture of volatile oils described above may be incorporated.

The composition may comprise from 1% to 15% by mass or from 1% to 10% by mass of one or more silicone or hydrocarbon-based nonvolatile oils, the primary function of which is to disperse the solid particles, notably the pigments, when the composition contains any.

The silicone oils may be chosen from phenyl silicone oils, for instance phenyl trimethicones, phenyl dimethicones, phenyltrimethylsiloxydiphenylsiloxanes, diphenyl dimethicones and diphenylmethyldiphenyltrisiloxanes.

The nonvolatile silicone oil that may be used in the invention may be chosen notably from polydimethylsiloxanes (PDMSs) with a viscosity of greater than 10 centistokes (cSt), PDMSs including alkyl, hydroxyl or alkoxy groups and polyalkylmethylsiloxanes.

The composition may also comprise a nonvolatile hydrocarbon-based oil known to those skilled in the art, although it is preferred to dispense with same in the context of the present invention.

It is preferred for the composition to contain 1% to 15% by mass of a nonvolatile silicone oil, such as a phenyl trimethicone.

Besides the ingredients described previously, the composition of the invention may comprise at least one cosmetically acceptable excipient which may be chosen from fragrances, biologically active agents intended to improve the appearance of the skin, oil-gelling agents, dyes, sweeteners to mask the bitterness of certain compounds, and preserving agents.

As examples of oil-gelling compounds that may be used in the context of the invention and that increase the viscosity of one of the oils mentioned previously, mention may be made of modified natural micas such as aluminum magnesium potassium fluorosilicate; organomodified clays which are clays treated with compounds chosen notably from quaternary amines, tertiary amines; fumed silicas surface-treated with a silicone compound, and ethylcelluloses.

According to one of the aspects of the invention, the composition may satisfy one of the following characteristics or a combination of several of these characteristics:

comprise less than 2% by weight, preferably less than 0.5% by weight, more preferably less than 0.1% or even be free of silica aerogel (INCI name: Silica silylate) as described notably in U.S. Pat. No. 7,470,725. These aerogels are porous materials obtained by replacing the oil contained in a silica gel with air. Aerogels thus contain a large proportion of gas. Now, the inventors have found that it is possible to obtain a cosmetic composition having the texture reproducing that of a foam without it being necessary for it to contain a gas, which considerably facilitates the manufacturing process;

be obtained according to a process of manufacturing and of packaging in a container, which process does not necessarily comprise a step of injecting a gas after mixing the ingredients mentioned above, the gas possibly representing between 30% and 65% by volume of the volume of cosmetic product into which it is desired to inject a gas. Such a gas is chosen, for example, from argon, helium, dinitrogen, nitrogen oxide, dioxygen, carbon dioxide, butane or propane. Preferably, the process for preparing the composition of the invention does not comprise a step of injecting gas;

comprise less than 5% by weight of compounds containing free OH groups such as silica, for example;

comprise less than 1% by mass, preferably less than 0.5%, or even be free of solid fatty compound(s) or of fatty compound(s) comprising a solid phase, such as waxes or pasty compounds. Mention will be made notably, as solid fatty compound, of stearic acid, a polyethylene wax, a synthetic wax, a paraffin wax or a microcrystalline wax, cetyl alcohol, stearyl alcohol, behenyl alcohol and glyceryl stearate. These compounds may in point of fact increase the sensation of tackiness and reduce the sensation of lightness that the film of composition generates on the skin;

comprise less than 15% by mass, preferably less than 10%, or even less than 2% by mass, and preferably be free of nonvolatile hydrocarbon-based oils. Mention may also be made of aliphatic esters such as esters of low molecular mass comprising from 10 to 40 carbon atoms, for example isononylisononanoate, fatty acid monoesters such as butyl isostearate, fatty alcohols such as 2-octyldodecanol. Among the hydrocarbon-based oils, mention may also be made of oils consisting of carbon and hydrogen, such as hydrogenated polyisobutene, liquid paraffin and squalene;

comprise less than 0.5% by mass of organic sunscreens, since these agents considerably reduce the sensory qualities of the composition.

According to one of the aspects described previously, the composition of the invention may serve as a base for a product for making up facial skin or the eyelids. The composition of the invention may be in the form of a facial skin makeup product (foundation) or of an eyelid makeup product (eyeshadow).

It may also serve as a base for a product for caring for the skin of the face, the neck or the contour of the eyes (lotion, serum, cream) or a makeup base for hiding skin imperfections or for conveying active agents.

According to a second aspect, the invention relates to a process for caring for or making up the skin, which consists in applying to the skin of the face, the neck or the eyelids a composition as described previously.

All the features that have been described in relation with these compositions apply to the makeup process of the invention.

In one embodiment, the process comprises a step of handling the composition by a user, the handling preferably being performed with the fingers or the hand. The handling step has the advantage of not destroying the texture of the composition when it is deposited on the skin. In a subsequent step, the user spreads the foam deposited on the skin using the fingers, the hand or an application means. The composition which has been deposited in the form of a foam, for example, then transforms into a matt film with a powdery effect which covers the skin by means of the spreading action.

The fraction of composition taken up from the container by the user may advantageously have the texture of a foam during the handling, and during the deposition of the fraction prior to spreading on the skin. On spreading the foam deposited on the skin, the composition changes in texture and forms a film essentially free of an oil which covers the area of skin concerned. The term "essentially free of" means a content of less than 15%, preferably less than 12%.

Preparation Process

Finally, the invention describes a process for manufacturing one of the compositions described previously.

According to a preferential embodiment, the crosslinked silicone polymer and/or the organomodified clay are provided in the form of a gel (or a dispersion) in an oil, before being mixed with the other compounds included in the composition of the product of the invention.

Thus, according to a particular embodiment, the manufacturing process is characterized in that it comprises a step of preparing or providing a gel of silicone polymer in a volatile oil, preferably isododecane, and also a step of manufacturing or providing a gel of organomodified clay in a volatile oil, preferably isododecane.

For example, the silicone polymer gel comprises gelled particles of crosslinked silicone polymer trapping molecules of a solvent, which solvent may represent between 10% and 95% by mass of the mass of the gel. The proportion of solvent contained in the gel may range from 60% to 95% by weight, for example from 80% to 90% by weight. The silicone polymer gel may be manufactured by applying a high shear to crosslinked silicone polymer particles in the presence of a solvent for the polymer. The shear may be produced in a high-pressure homogenizer, so as to obtain gelled polymer particles whose size ranges between 10 and 200 microns.

Reference will be made equivalently to a gel of crosslinked silicone polymer in a solvent or to crosslinked silicone polymer particles gelled with a solvent.

The solvent for the polymer which makes it possible to gel it is preferably a volatile oil described previously, for example isododecane.

In a particular embodiment, the process of the invention will comprise a step of providing a gel of crosslinked silicone polymer in a volatile oil, a step of providing a gel of organomodified clay in a volatile oil, and a step of mixing the crosslinked silicone polymer gel and the organomodified clay gel so as to form a premix. In a step subsequent to the preceding steps, the premix may optionally be mixed with an amount of one or more volatile oils, which may be identical to the solvent for the polymer or to the solvent contained in the organomodified clay gel, which were used for the preparation of the premix.

The premix may also be mixed, where appropriate, with other ingredients, such as solid particles, film-forming polymers and non oils. Solid particles such as pigments or fillers with an optical effect may be added to prepare a composition intended for caring for or making up the skin.

In a final step, the cosmetic composition consisting of the ingredients described above may be packaged in a container equipped with a closure means such as a cylindrical jar or a tube.

The process of the invention makes it possible to obtain a product whose texture is similar to that of a foam, without necessarily performing a step of injecting gas after the step of mixing the ingredients, and before the step of packaging the composition in a container.

The invention moreover describes a foundation product for making up the face, which is packaged in a bottle or in a tube having an orifice that is wide enough so as not to destroy the texture of the foam at the time of removing the product. A packaging comprising an application means integral to a container such as a brush or a pencil is unsuitable for dispensing the product, since there would be a risk of it fluidizing the foam before it is spread on the skin by the user.

The invention is illustrated in greater detail by the examples that follow. The mixture of all the ingredients is preferably prepared with stirring, at atmospheric pressure and at low temperature, for example at 30° C., 25° C. or 20° C.

Examples

The products whose mass composition is indicated in table 1 were prepared.

TABLE 1

| INCI name or chemical name | Example 1 | Comparative example 1 | Comparative example 2 |
|---|---|---|---|
| | | Mass % | |
| Polysilicone-11 (Gransil ® PC-12) | 3.6 | 4.9 | — |
| Dimethicone/vinyldimethicone crosspolymer (KSG-16 ®) | — | — | 3.6 |
| Disteardimonium hectorite | 1.3 | — | 1.3 |
| Propylene carbonate | 0.4 | — | 0.4 |
| Trimethyl siloxysilicate | 2.0 | 2.0 | 2.0 |
| Phenyl trimethicone | 10.0 | 10.0 | 10.0 |
| Methyl methacrylate crosspolymer | 6.1 | 6.1 | 6.1 |
| Synthetic fluorophlogopite | 2.4 | 2.4 | 2.4 |
| Pigments | 10.0 | 10.0 | 10.0 |
| Volatile solvents | qs 100 | qs 100 | qs 100 |

Manufacturing Process

The organomodified hectorite is dispersed in the volatile solvents in the main beaker, with stirring using a Rayneri blender. When the phase is homogeneous, the propylene carbonate is added thereto until a homogeneous gel is obtained.

The polysilicone-11 or the dimethicone/vinyldimethicone crosspolymer is then added to this mixture. The mixture is homogenized by stirring using a Rayneri blender until it is visually homogeneous.

In a secondary beaker, the pigments are dispersed in the phenyl trimethicone in a three-roll mill (3 treatments in the three-roll mill). This pigment dispersion is added to the main beaker, and the mixture is then homogenized with stirring using a Rayneri blender until it is visually homogeneous.

The other ingredients are added and the mixture is stirred using a Rayneri blender until the whole is visually homogeneous.

Stability Study

The foundation compositions of each of the examples are placed in an oven at 25° C. for 24 hours.

Results: The results are presented in table 2 below. The product of example 1 according to the invention is stable, whereas the products of comparative examples 1 and 2 undergo phase separation.

Measurement of the Viscosity and Texture

The viscosity of example 1 is measured with a Rheolab QC (Anton Paar) viscometer equipped with the Rheoplus software.

The viscosity of comparative examples 1 and 2 is measured with the blade spindle rotating at 50 rpm for 3 minutes, whereas the viscosity of example 1 according to the invention is measured with the anchor spindle (ST22-2V) rotating at 10 rpm for 7 minutes.

Prior to the measurement, each composition is poured into a 120 ml jar (Ref: 102171001, Kola Rond VT3 M120 Blanc Pharm) and then placed in an oven at 25° C. for a minimum of 12 hours. Once the spindle has been inserted in the jar, the level of composition reaches the neck of the jar.

The viscosity value is equal to the mean of the last fifteen measurements taken by the machine over the measuring time indicated above.

Results:

The results are presented in table 2 below. The composition of the invention has the texture of a foam with a granite appearance at the surface, which does not flow when the jar is turned upside-down, whereas the composition of comparative example 1 and of comparative example 2 have the texture of a thick fluid which spreads quite rapidly over a flat surface.

TABLE 2

|  | Example 1 | Comparative example 1 | Comparative example 2 |
| --- | --- | --- | --- |
| Appearances | Firm, matt foam | Thick glossy fluid | Thick glossy fluid |
| Viscosities measured (mPa · s) | 230 000 | 22 000 | 18 000 |
| Stabilities 24 h | YES | NO - Phase separation | NO - Phase separation |

In-Vivo Self-Evaluations

The product of example 1 of the invention was evaluated by a panel in absolute terms, under a blind test, for a period of use of one week according to the instructions for use supplied. The panel consisted of 65 women from 20 to 50 years old, equitably distributed, regularly using a prior art foundation corresponding to that described in the MINTEL sheet No. 10174267.

The following is a summary of the assessments that were collected. It was checked that the mean of the numerical values obtained is significant.

Overall Assessment:
 Very good satisfaction: 98% "satisfied"
 Very firm intentions to purchase: 94% purchase
 Preference for the test product: 60%, preference for the usual product: 15%, and no preference: 25%.

Spontaneous Assessment:

Spontaneously, all the women made at least one positive comment with regard to the foundation and the criticisms are minor. The product is assessed for:
 its makeup result: uniform, natural, beautiful/pretty, covering, luminous result, which stays on well
 its skin finish: no sensation of heaviness, soft, comfortable and above all non-shiny skin
 its texture: very light, pleasant, subtle and soft
 its very easy application Texture:

The product has highly appreciated cosmeticity:
 a pleasant texture (100%, 89% "very pleasant"),
 a soft texture (100%, 86% "very soft"),
 a light texture (100%, 71% "very light"), fine (98%, 57% "very fine"), with a very well equilibrated consistency (91% "just as it should be")

Application:

Very easy application (97%, 85% "very easily"), very quick (97%, 79% "very quickly"), very uniform (97%, 71% "very uniform"), no boundary lines (98%), no accumulation in the skin reliefs (97%) or streaks (95%) and no pilling (100%)

Makeup Result:

Very good makeup result:
 Skin that is not shiny (on application: 98%; a few moments later: 95%), not tacky (100% on application and a few moments later) and which remains very comfortable throughout the day (100%, of which 75% "very comfortable")
 A very well-unified complexion (Top2: 98%, 78% "very good") with good coverage (86% "just as it should be"), a finish that is both matt (48%) and powdery (41%) with a rather natural look (59%) and having very good persistence (~9 h overall; ~8 h for the matt effect).

Image Profile:

Above all, the makeup film is fine, without any mask or matter effect, the complexion is rendered matt, totally unified, the skin appears more beautiful, smoother, the areas of dryness are not pronounced and the color does not change, it remains homogeneous ("entirely in agreement">60%).

The complexion is also enhanced, luminous, "perfect", well-corrected, the pores are less visible, the skin grain is refined, the makeup is matt but radiant and the foundation persists well and the matt effect is long-lasting ("entirely in agreement" ~55%-45%).

In conclusion, the product of the invention allows a very light application combined with high coverage which efficiently hides skin imperfections, while at the same time affording highly appreciable comfort on application which lasts over time.

The invention claimed is:

1. A cosmetic foundation composition for caring for and making up the skin, in the form of a foam comprising:
 from 35% to 75% of at least one volatile oil,
 from 1% to 6% of a polysilicone-11,
 from 0.5% to 5% of an organomodified clay, and
 less than 5% of water,
the mass ratio between the polysilicone-11 and the organomodified clay being between 1/1 and 10/1, and the percentages being expressed on a mass basis relative to the mass of said composition, said foam having a viscosity at 25° C. and atmospheric pressure between 50,000 and 500,000 mPa·s, and a density at 25° C. and atmospheric pressure between 0.8 and 1.2 g/cm$^3$.

2. The composition as claimed in claim 1, wherein the organomodified clay is an organomodified hectorite modified with a quaternary alkylammonium chloride.

3. The composition as claimed in claim 1, wherein the composition comprises from 1% to 10% by mass of a silicone resin relative to the mass of said composition.

4. The composition as claimed in claim 1, wherein the volatile oil is isododecane.

5. The composition as claimed in claim 1, wherein the composition comprises from 10% to 30% of solid particles.

6. A process for caring for or making up the skin, which comprises applying to facial skin a composition as claimed in claim 1.

7. A process for preparing the composition as claimed in claim 1, comprising preparing or providing a gel of polysilicone-11 in a volatile oil, also preparing or providing a gel of organomodified clay in a volatile oil, and mixing the gel of polysilicone-11 and the gel of organomodified clay.

* * * * *